United States Patent
Calame

(10) Patent No.: US 6,389,894 B1
(45) Date of Patent: May 21, 2002

(54) METHOD FOR DETERMINING THE HEIGHTS OF MULTIPLE JUMPS

(75) Inventor: Christian Calame, Winterthur (CH)

(73) Assignee: K.K. Holding AG, Winterthur (CH)

( * ) Notice: Subject to any disclaimer, the term of this patent is extended or adjusted under 35 U.S.C. 154(b) by 42 days.

(21) Appl. No.: 09/640,757

(22) Filed: Aug. 18, 2000

(30) Foreign Application Priority Data

Aug. 24, 1999 (CH) ............................. 1543/99

(51) Int. Cl.$^7$ .............. A61B 5/22; A61B 5/00; G01P 7/00; G01M 7/00
(52) U.S. Cl. ............ 73/379.01; 73/503; 73/12.01; 73/172
(58) Field of Search ............... 73/172, 379.01, 73/379.04, 12.01, 862.381, 503

(56) References Cited

U.S. PATENT DOCUMENTS

| | | |
|---|---|---|
| 3,504,540 A | 4/1970 | Pradko et al. |
| 3,894,437 A | 7/1975 | Hagy et al. |
| 4,136,682 A | 1/1979 | Pedotti |
| 4,928,959 A | 5/1990 | Bassett et al. |
| 5,029,483 A | 7/1991 | Gautschi et al. |
| 5,186,062 A | 2/1993 | Roost |
| 5,299,454 A | 4/1994 | Fuglewicz et al. |
| 5,469,740 A | 11/1995 | French et al. |
| 5,574,669 A | 11/1996 | Marshall |
| 5,838,638 A * | 11/1998 | Tipton et al. .................. 368/10 |
| 5,897,457 A * | 4/1999 | Mackovjak .................... 482/8 |
| 5,913,242 A | 6/1999 | Stüssi |

* cited by examiner

*Primary Examiner*—Hezron Williams
*Assistant Examiner*—Katina Wilson
(74) *Attorney, Agent, or Firm*—Barnes & Thronburg

(57) ABSTRACT

Comparable values for the heights of the individual jumps in a series of multiple jumps can be achieved, if defined initial conditions for first and second successive integrations of measured vertical forces are given for each individual jump. The initial condition for the first integration is taken as a zero velocity in the middle of the flight time interval for each individual jump. For every second integration, as initial condition for the jump height, a constant initial height is taken. This is a characteristic value of the test person.

11 Claims, 3 Drawing Sheets

| G | ha |
|---|---|
| < 1.60m | 0.09m |
| 1.60 ... < 1.70m | 0.10m |
| 1.70 ... < 1.80m | 0.12m |
| ≥ 1.80m | 0.14m |

METHOD FOR DETERMINING THE HEIGHTS OF MULTIPLE JUMPS

BACKGROUND AND SUMMARY OF THE INVENTION

The invention concerns a method of determining height of a series of jumps by double integration.

In rehabilitation therapy and the training of athletes, jumping force measurements are very important for performance diagnostics, for ascertaining the efficiency of the legs with regard to speed, coordination and endurance. For this both individual and multiple jumps are measured, the latter involving a series of jumps in immediate succession.

Measuring the vertical jumping force of the legs is accomplished with measuring platforms such as those covered by U.S. Pat. No. 5,913,242. Derived from this can then be a number of parameters like the jumping height and jumping performance. Fitted in the feet of such measuring platforms are force sensors which measure the jumping force continuously, transmitting within one second a large number—typically several hundred—measured values to an evaluation facility such as computer. From this the measured results are plotted in the form of force curves for example.

From the shape of a measured curve the heights of a jump can be calculated by integrating twice. It is advantageous to define the time interval of a jump from standstill before the jump to renewed standstill after it. For determining the height of a single jump this method yields good results. With multiple jumps it fails, however, because the critical values of the starting conditions for the accelerations in the first integration and for the velocity in the second integration depend on the final conditions of the previous jump. With multiple jumps, small measuring and integration errors add up so seriously that the jump heights can no longer be calculated clearly and satisfactorily, leading to completely unusable results especially with longer series of jumps.

The object of the invention is to overcome this disadvantage when determining the heights of multiple jumps. It is achieved through the features in the present invention. With the invention, defined initial conditions are fixed for the acceleration and velocity for both integrations of each individual jump in a series of jumps. Through these starting conditions the small integration errors are eliminated in each case.

Advantageous refinements and enhanced precision of the new method take into account the special features of the first and last jump in a multiple jump series.

The time intervals selected for determining the standstill of a test person before the first and last jump may be typically 200 ms. Within these time intervals the following conditions must likewise be satisfied as "preset fluctuation ranges":

a) Within the selected time interval the average measuring signal must exceed 0.5 times the body weight, and
b) the standard deviation of the signal must not exceed 5% of the body weight within the selected time interval.

Condition a) ensures that the test person is really standing on the measuring platform, while condition b) ensures that he is standing relatively still. Of course other values and criteria may be taken for standing on the platform and for the "rest" position.

Below the invention will be explained in more detail with reference to a typical embodiment and some drawings.

Other objects, advantages and novel features oft he present invention will become apparent from the following detailed description of the invention when considered in conjunction with the accompanying drawings.

DETAILED DESCRIPTION OF THE PREFERRED EMBODIMENTS

Figure 4:
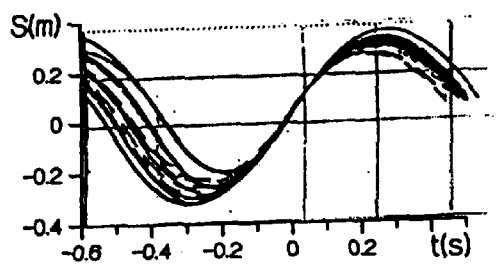
FIG. 4 shows typical anthropometric relations between initial height ha and body size G of the jumper.

In the typical embodiment that follows, the heights of a series of 18 jumps performed by a healthy young man are determined. His body size was 1.72 m, which according to the table in FIG. 4 gives an initial height ha of 0.12 m.

Figure 3:
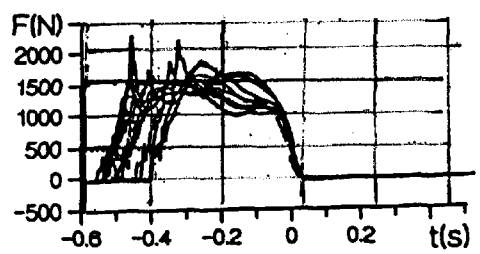
FIG. 3 shows the plots and evaluation of the typical embodiment described below.
Figure 3:
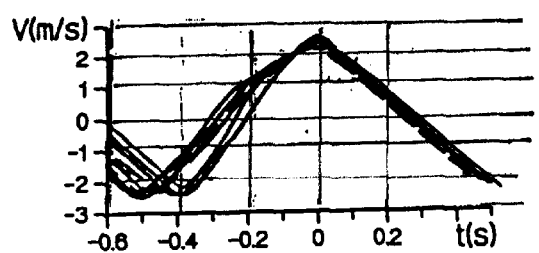

The force curves were recorded with a measuring platform according to the mentioned US patent, and the measured values of the force sensors were transmitted to a data processing facility which processed the measured values with the help of known methods and plotted them in the form of the curves in FIG. 3. The top diagram of FIG. 3 plots the force at the individual jumps of the series in newtons (N), with the time t0 of jumping-off at each jump shifted into the zero of the horizontal time axis, so that the curves of the individual jumps are overlaid. The middle diagram plots the curves for velocity $\underline{v}$ in metres per second (m/s) calculated from the force curves using the method according to the invention. Plotted in the bottom diagram of FIG. 3 are the heights $\underline{s}$ in metres (m) of the individual jumps. The curves reveal closely congruent heights for the individual jumps in a series, all of them inside a narrow time interval.

Figure 1:
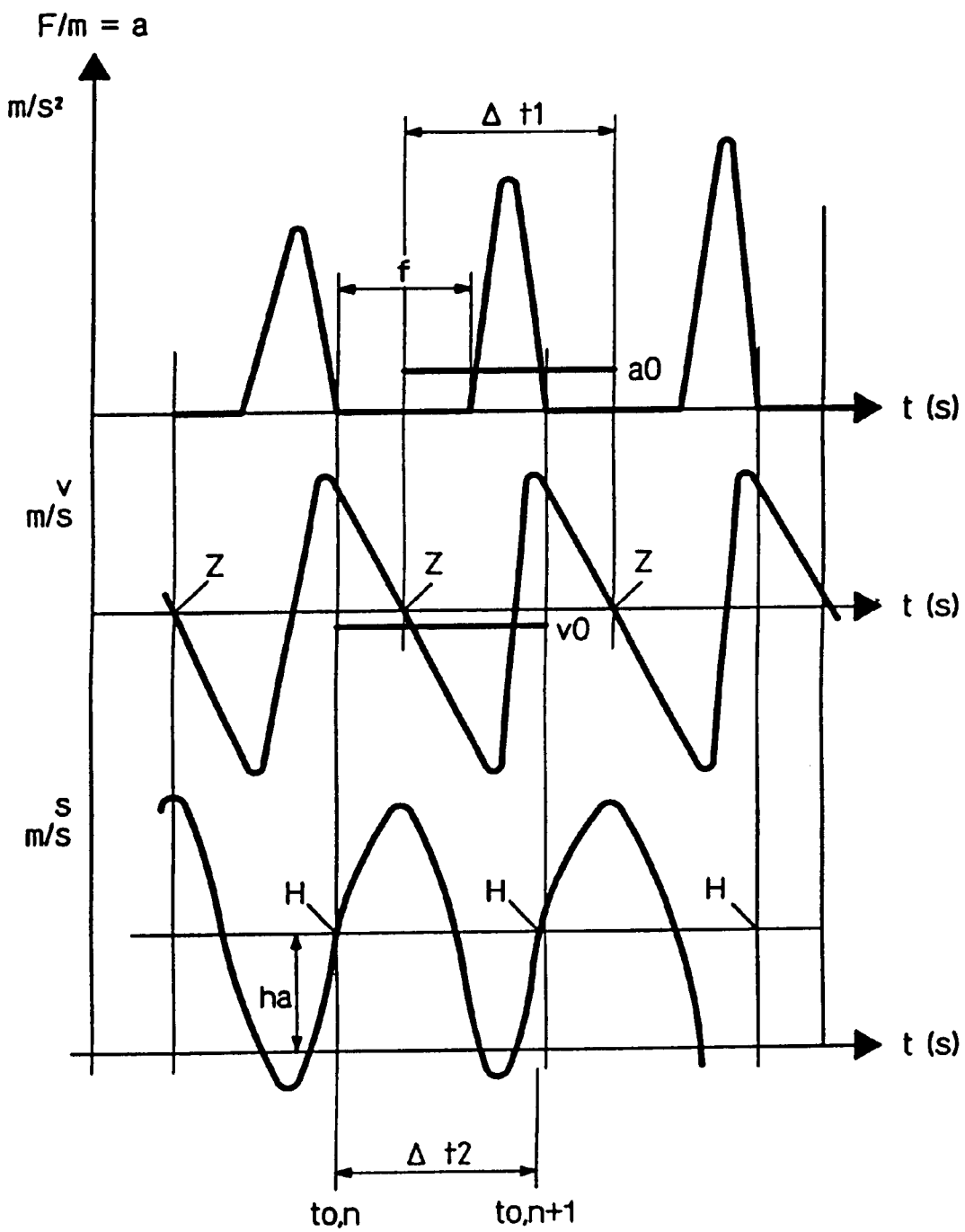
FIG. 1 shows purely schematically an excerpt from the force curve for a multiple jump and the integrations derived from it for the velocity and jump height using the new method according to the principles of the present invention.

FIG. 1 serves to explain the new method and show the various parameters used. It shows schematically, again in three diagrams one above the other, an excerpt from a series of successive jumps. Plotted in the top diagram against time $\underline{t}$ are the accelerations $\underline{a}$ in metres per second$^2$ (m/s$^2$) calculated from the measured vertical forces, below this the velocities $\underline{v}$ in m/s obtained after the first integration and the jump heights $\underline{s}$ in m determined with the help of the second integration.

A comparison of the two schematic curves in FIG. 1 for $\underline{a}$ and $\underline{v}$ reveals that in the middle of each flight phase $\underline{f}$ the velocity $\underline{v}$ as required according to the invention is zero (point Z in the velocity plot.) For the first integration therefore, there is at each individual jump a time interval $\Delta t1$ from one flight phase middle to the next. If a mean value is calculated for all accelerations during the same time interval $\Delta t1$, the initial condition a0 for the first integration emerges for each individual jump; in the top diagram of FIG. 1, a value for a0 is entered by way of example.

For the second integration, the height $\underline{s}$ of each individual jump is calculated from the curve for the velocity $\underline{v}$ obtained from the first integrations: A time interval $\Delta t2$ is fixed at each individual jump, extending from the jump-off t0.n till the next jump-off t0.n+1, which will be evident from a comparison of the two outer diagrams of FIG. 1.

According to the invention, this integration step begins for each individual jump; at a point H (FIG. 1) which lies above the zero line for the jump height $\underline{s}$ displaced by the initial height ha. (Like the acceleration a0, the initial condition v0 for integrating the velocity curve is determined by a mean value of all velocities of the particular individual jump. For an individual jump a starting condition v0 is entered by way of example in the middle diagram of FIG. 1.) As already mentioned, the simplest way to determine the initial height ha is to take it as anthropometric constant from a table like that in FIG. 4, for example. Evaluation of the multiple jump series according to FIG. 3 is based on a constant of this kind for ha.

Figure 2:
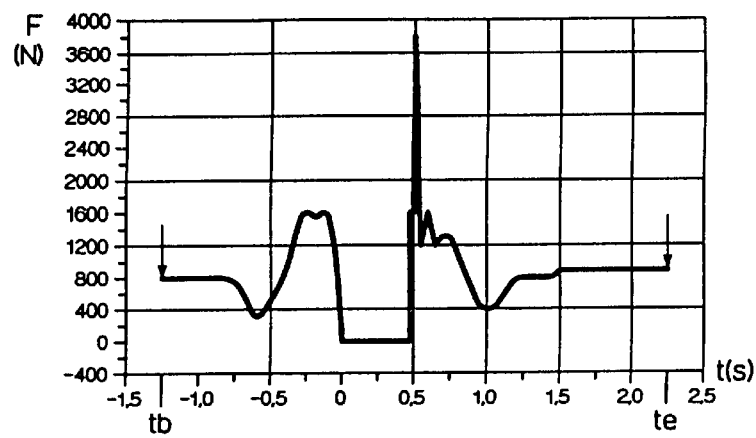
FIG. 2 plots the curves for the measured force and the velocity derived from it, as well as the height of an individual jump, from which the initial height may be determined.
Figure 2:
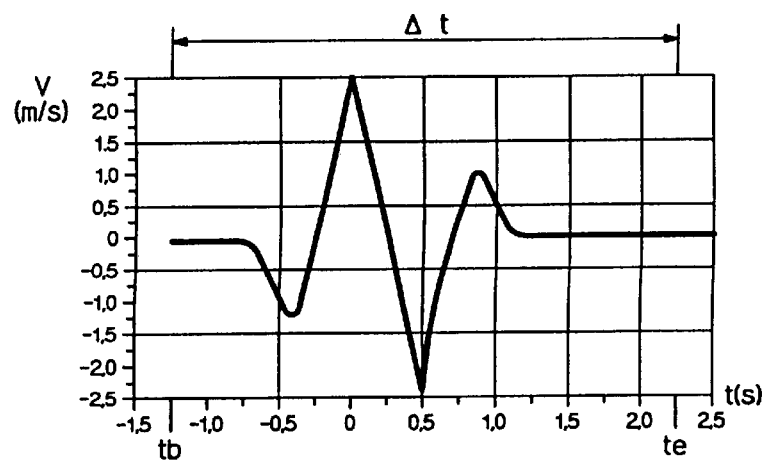
Figure 2:
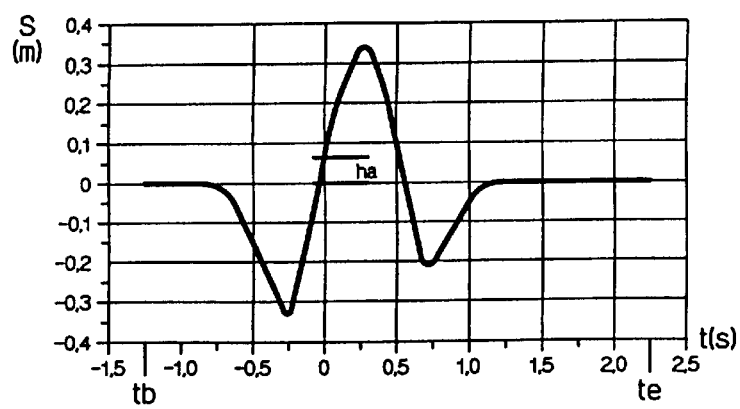

A more accurate determination of the value of ha, adapted individually to the jumper, is obtained from an evaluation of an individual jump as shown in FIG. 2. Plotted in the three diagrams arranged one above the other are the measured vertical force in newtons for a single jump and the velocity v in m/s derived from it, as well as the jump height s in m. The initial height ha sought then emerges from the bottom diagram as the jump height s at the time t=0, i.e. at the time of jumping-off. With this experimental, individual determination of ha, it is possible not only to allow for differences of this value between different test persons of almost identical body size, but also to take into account different "conditions" of the same test person at different times, in a single jump and/or after a series of multiple jumps. Of course a number of individual jumps also may be used for a mean calculation of ha.

Special features are displayed by the first and last individual jump in a series, because their time interval does not begin or end in the middle of a flight time or at a jump-off t0.n but begins or ends at the time tb or te of a standstill. The beginning or end of a standstill may be fixed in the manner described for example by predetermined fluctuation ranges of the measured values during preselected times. Of course, the same criteria hold true for defining a standstill after a single jump according to FIG. 2.

In contrast to the integrations of a "mean" jump in a series, the different time interval Δt2.1 at the first individual jump may be taken into account for the second integration, i.e. for calculating the jump height s. This includes proceeding not from the initial height ha but from a zero value for the jump height s, and by subtracting the quotient of initial height ha and time interval (Δt2.1) for the first jump—i.e. from tb till the first jump-off t0.1—from the mean velocity value v(t) calculated to determine the initial condition v0 for the velocity.

The special nature of the last jump affects only the determination of the initial velocity v0 for the second integration. For the last jump therefore, the quotient of initial height ha and time interval Δt2.e of the last jump may be added to the mean value v(t), i.e. from the last jump-off to.e till standstill te.

With the new method for evaluating measured vertical forces in multiple jumps, comparable values are obtained for the heights of individual jumps, allowing assessment of performance progress after injuries and during rehabilitation, also when training individual test persons, or of differences in jumping force between different persons.

Although the present invention has been described and illustrated in detail, it is to be clearly understood that the same is by way of illustration and example only, and is not to be taken by way of limitation. The spirit and scope oft he present invention are to be limited only by the terms of the appended claims.

What is claimed is:

1. A method for determining the heights of a series of immediately successive jumps, so-called multiple jumps, by twice integrating by time accelerations determined from measured vertical forces, characterized by the force curve of each individual jump being integrated twice under the following boundary conditions:
    a) at each first integration, an acceleration integral is calculated starting from a velocity in the middle of the flight time interval which velocity is taken as zero, and
    b) at each second integration, a velocity integral is calculated starting from a constant initial height at the time of jumping.

2. The method according to claim 1, wherein a mean value of the accelerations of the particular jump is taken as starting condition for the acceleration at each individual jump for every first integration.

3. The method according to claim 2, wherein the mean value of the velocities of the individual jump is selected as an initial velocity for every second integration.

4. The method according to claim 3, wherein the initial height is disregarded at the second integration of the first jump in a series, and its quotient with the time interval up to first jump-off is deducted from the mean value of velocity under the starting condition for the velocity.

5. The Method according to claim 4, wherein the starting instant of the time interval of the first jump is fixed when the measured values within a preselected time period lie inside a predetermined fluctuation range.

6. The method according to claim 3, wherein the starting height as a quotient with the_time_integral of the last jump is added to the mean value of velocity under the starting condition for the velocity for the second integration of the last jump in a series.

7. The method according to claim 6, wherein the end of the time interval of the last jump in a series is fixed when the measured values within a preselected time period lie inside a predetermined fluctuation range.

8. The method according to claim 1 wherein the initial height is determined by evaluation of an individual jump.

9. The method according to claim 1 wherein the initial height is determined as an anthropometric variable depending on body size of the jumper.

10. The method according to claim 1, wherein a mean value of velocities of the individual jump is selected as an initial velocity for every second integration.

11. The method according to claim 1, wherein the first integration is taken between middle of flight time intervals of two individual jumps.

* * * * *